United States Patent [19]

Fernandez et al.

[11] Patent Number: 5,015,656

[45] Date of Patent: * May 14, 1991

[54] ORGANIC COMPOUNDS AND THEIR USE AS PHARMACEUTICALS

[75] Inventors: Maria I. F. Fernandez, Madrid, Spain; Terrence M. Hotten, Farnborough; David E. Tupper, Reading, both of England

[73] Assignees: Lilly S.A., Madrid, Spain; Lilly Industries Limited, Basingstoke, England

[*] Notice: The portion of the term of this patent subsequent to Feb. 27, 2007 has been disclaimed.

[21] Appl. No.: 412,691

[22] Filed: Sep. 26, 1989

[30] Foreign Application Priority Data

Sep. 30, 1988 [GB] United Kingdom ............... 8823041

[51] Int. Cl.$^5$ ............... A61K 31/38; C07D 405/00; C07D 409/00; C07D 333/22
[52] U.S. Cl. ............... 514/422; 514/414; 514/444; 514/445; 514/447; 514/448; 514/326; 544/145; 544/379; 546/207; 546/208; 546/209; 546/210; 546/211; 546/212; 548/262.2; 548/336; 548/374; 548/527; 549/55; 549/63; 549/64; 549/76
[58] Field of Search ............... 548/262, 527, 336, 374; 514/422, 445, 444, 451, 414, 448, 326; 549/76, 55, 63, 64; 546/212, 208, 211, 207, 210, 209; 544/145, 379

[56] References Cited

U.S. PATENT DOCUMENTS

| | | | |
|---|---|---|---|
| 3,177,252 | 4/1965 | Thominet | 260/559 |
| 3,342,826 | 9/1967 | Miller et al. | 260/294 |
| 3,932,503 | 1/1976 | Weber et al. | 260/553 DA |
| 4,123,550 | 10/1978 | Untch et al. | 424/275 |
| 4,221,815 | 9/1980 | Weyer et al. | 424/319 |
| 4,321,378 | 3/1982 | Dostert et al. | 544/321 |
| 4,382,929 | 5/1983 | Bradshaw et al. | 514/422 |
| 4,560,751 | 12/1985 | Seybold | 544/60 |
| 4,777,179 | 11/1988 | Bradshaw et al. | 546/267 |
| 4,904,686 | 2/1990 | Fernandez et al. | 514/422 |

FOREIGN PATENT DOCUMENTS

| | | |
|---|---|---|
| 14705 | 10/1988 | Australia . |
| 60235 | 9/1982 | European Pat. Off. . |
| 65295 | 11/1982 | European Pat. Off. . |
| 170024 | 2/1986 | European Pat. Off. . |
| 171739 | 2/1986 | European Pat. Off. . |
| 297697 | 1/1989 | European Pat. Off. . |
| 1937759 | 9/1970 | Fed. Rep. of Germany . |
| 2952279 | 6/1981 | Fed. Rep. of Germany . |
| 63267778 | 11/1958 | Japan . |

OTHER PUBLICATIONS

Consiglio et al., *J. Chem. Soc. Perkin Trans. II*, 1983, 1559-61.
C.A. 72, 3226a (1970).
C.A. 67, 2167w (1967).
C.A. 101, 122562j (1984).
C.A. 100, 84964m (1984).
Anales de la Real Academic de Pharmacia, 42, (4), 563 (1976), (Chemical Abstracts 87: 23197e).
Anales de Quimica, 70 (12), 974, (1974), (Chemical Abstracts 83: 178980w).

Primary Examiner—Frederick E. Waddell
Assistant Examiner—Celia Chang
Attorney, Agent, or Firm—Robert A. Conrad; Leroy Whitaker

[57] ABSTRACT

A pharmaceutical compound of the formula

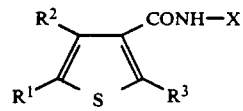

in which $R^1$, $R^2$ and $R^3$ independently are hydrogen, hydroxy, halo, nitro, amino, $C_{2-5}$ acylamino, $C_{1-4}$ alkyl, —CHO, —CH$_2$OH, —CH$_2$OC$_{1-4}$ alkyl, —COOH, —COC$_{1-3}$ alkyl, —CH(OH)C$_{1-3}$ alkyl, $C_{1-4}$ alkoxy, $C_{2-4}$ alkenyloxy, $C_{1-4}$ alkylthio, $C_{1-4}$ alkylsulphinyl, $C_{1-4}$ alkylsulphonyl, N-substituted heterocyclyl, optionally substituted phenyl, optionally substituted phenylthio, optionally substituted phenylsulphinyl, optionally substituted phenylsulphonyl or optionally substituted phenylsulphonamido, or $R^1$ and $R^2$ together form a $C_{3-5}$ alkylene bridge; provided that at least one of $R^2$ and $R^3$ is $C_{1-4}$ alkoxy or $C_{2-4}$ alkenyloxy; and X is (i) —(CH$_2$)$_n$N(R$^4$)$_2$ where each $R^4$ independently is $C_{1-4}$ alkyl, $C_{2-4}$ alkenyl or optionally substituted $C_6H_5CH_2$—, and n is 1, 2 or 3, or (ii) a 5- to 8-membered alicyclic group containing one or two nitrogen atoms and directly attached to the amido nitrogen or attached by a $C_{1-3}$ alkylene chain; and salts and esters thereof.

5 Claims, No Drawings

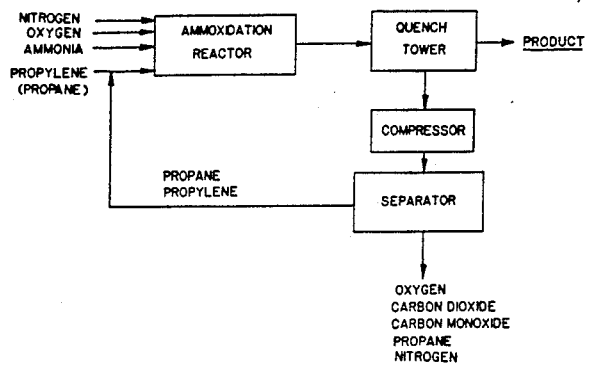

ORGANIC COMPOUNDS AND THEIR USE AS PHARMACEUTICALS

This invention relates to organic compounds and their preparation and use as pharmaceuticals.

The compounds of the invention are of the formula

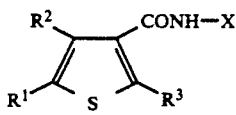
(I)

in which $R^1$, $R^2$ and $R^3$ independently are hydrogen, hydroxy, halo, nitro, amino, $C_{2-5}$ acylamino, $C_{1-4}$ alkyl, —CHO, —$CH_2OH$, —$CH_2OC_{1-4}$ alkyl, —COOH, —$COC_{1-3}$ alkyl, —$CH(OH)C_{1-3}$ alkyl, $C_{1-4}$ alkoxy, $C_{2-4}$ alkenyloxy, $C_{1-4}$ alkylthio, $C_{1-4}$ alkylsulphinyl, $C_{1-4}$ alkylsulphonyl, N-substituted heterocyclyl, optionally substituted phenyl, optionally substituted phenylthio, optionally substituted phenylsulphinyl, optionally substituted phenylsulphonyl or optionally substituted phenylsulphonamido, or $R^1$ and $R^2$ together form a $C_{3-5}$ alkylene bridge; provided that at least one of $R^2$ and $R^3$ is $C_{1-4}$ alkoxy or $C_{2-4}$ alkenyloxy; and X is (i) —$(CH_2)_nN(R^4)_2$ where each $R^4$ independently is $C_{1-4}$ alkyl, $C_{2-4}$ alkenyl or optionally substituted $C_6H_5CH_2$—, and n is 1, 2 or 3, or (ii) a 5- to 8-membered alicyclic group containing one or two nitrogen atoms and directly attached to the amido nitrogen or attached by a $C_{1-3}$ alkylene chain; and salts and esters thereof.

When X is an alicyclic group it is preferably attached at one of its carbon atoms and can contain an additional hetero atom as in a morpholino group or two nitrogen atoms as in piperazino, but preferably it contains only a single nitrogen atom. When the alicyclic group is attached via an alkylene chain, the chain is preferably of the form —$(CH_2)_n$—where n is 1, 2 or 3 and X is thus of the formula —$(CH_2)_nY$ where Y is an alicyclic ring attached at one of its carbon atoms. The alicyclic ring can be substituted by, for example, a $C_{1-4}$ alkyl, $C_{2-4}$ alkenyl or optionally substituted $C_6H_5CH_2$-group.

The following are preferred examples of alicyclic groups:

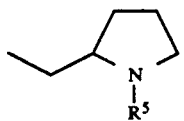

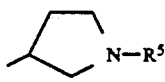

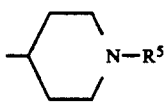

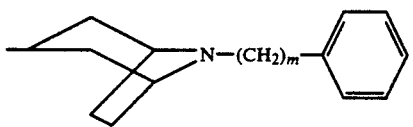

where m is 1, 2 or 3 and $R^5$ is $C_{1-4}$ alkyl, $C_{2-4}$ alkenyl or optionally substituted $C_6H_5CH_2$—.

The compounds of the invention and their pharmaceutically acceptable salts and esters have useful effects on the central nervous system.

When $R^1$, $R^2$ or $R^3$, in the above formula, is halo it is preferably fluoro, chloro or bromo, and especially chloro or bromo. When reference is made to $C_{1-4}$ alkyl this includes, for example, methyl, ethyl, n-propyl, isopropyl and butyl and is especially methyl or ethyl. The groups $C_{1-4}$ alkoxy, $C_{1-4}$ alkylthio, $C_{1-4}$ alkylsulphinyl and $C_{1-4}$ alkylsulphonyl consist of these alkyl groups attached to the thiophene ring through an oxygen, sulphur atom, sulphinyl (—SO—) or a sulphonyl (—$SO_2$—) group. The amino group is —$NH_2$ and the acylamino group of the formula RCONH— where R is preferably $C_{1-4}$ alkyl, a preferred example being acetylamino. When $R^1$, $R^2$ or $R^3$ is optionally substituted phenyl, phenylthio, phenylsulphinyl, phenylsulphonyl or phenylsulphonamido, it is preferably an unsubstituted phenyl, phenylthio, phenylsulphinyl, phenylsulphonyl and phenylsulphonamido group. If desired, however, the phenyl nucleus can be substituted with one or more, preferably one to three, substituents selected from, for example, halogen, $C_{1-4}$ alkyl, $C_{1-4}$ alkoxy, hydroxy, nitro, cyano, amino, carboxy and carboxamido. Examples of N-substituted heterocyclic substituents are imidazolyl, pyrazolyl and triazolyl attached through a nitrogen atom, and in particular 1-pyrazolyl and 1-(1,2,4-triazolyl).

When $R^4$ or $R^5$ is $C_{2-4}$ alkenyl, it is preferably vinyl or propenyl, and when $R^1$, $R^2$ and $R^3$ is alkenyloxy it is one such alkenyl group attached via an oxygen atom to the thiophene nucleus. When $R^4$ and $R^5$ is optionally substituted $C_6H_5CH_2$—, although preferably unsubstituted, it can be substituted on the phenyl group with, for example, one or more substituent as defined above.

A preferred group of compounds is one in which X takes the value defined in (ii) above, that is, X is a 5- to 8-membered alicyclic group, and X is most preferably a group of the formula

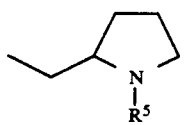

in which $R^5$ is $C_{1-4}$ alkyl, $C_{2-4}$ alkenyl or $C_6H_5CH_2$—.

The novel compounds of the invention are useful both as the free compound and as salts and esters. For example the pharmaceutically-acceptable acid addition salts such as salts derived from non-toxic inorganic acids, for example, hydrochloric acid, nitric acid, phosphoric acid, sulphuric acid, hydrobromic acid, hydroiodic acid and phosphorous acid, as well as salts derived from non-toxic organic acids such as aliphatic mono- and dicarboxylic acids, especially fumaric acid, phenyl-substituted alkanoic acids, hydroxyalkanoic and hydroxyalkandioic acids, aromatic acids, aliphatic and aromatic sulphonic acids. In addition to pharmaceutically-acceptable salts, other salts are included such as, for example, those with picric or oxalic acids; they may serve as intermediates in the purification of the compounds or in the preparation of other, for examples pharmaceutically-acceptable, acid addition salts, or are useful for identification, characterisation or purification of the bases.

Acid groups, such as COOH on the thiophene nucleus allow the formation of salts with bases. Examples of such salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, calcium hydroxide, methylamine, diethylamine, ethylene diamine, cyclohexylamine and ethanolamine. The potassium and sodium salt forms are particularly preferred. It is preferred that the salt is pharmaceutically-acceptable but, as explained above, other salts are also included in the invention. With regard to esters, these may be formed at the carboxyl group by conventional alcohols. Examples of such alcohols include alkanols of formula ROH where R is alkyl, preferably $C_{1-8}$ alkyl and especially methanol and ethanol. Thus the most preferred ester derivatives are the methyl and ethyl esters of the compounds of formula (I).

It will be appreciated that the compounds of the invention can contain one or more assymetric carbon atom which gives rise to isomers. The compounds are normally prepared as racemic mixtures and can conveniently be used as such but individual isomers can be isolated by conventional techniques if so desired. Such racemic mixtures and individual optical isomers form part of the present invention and it is preferred to use an enantiomerically pure form.

A preferred group of compounds according to the invention is of the formula

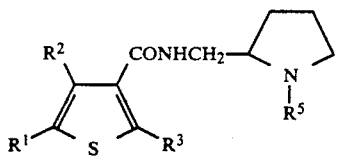

in which $R^1$, $R^2$ and $R^3$ independently are hydrogen, halo, —CHO, $CH_2OH$, $C_{1-4}$ alkyl, $C_{1-4}$ alkoxy or $C_{1-4}$ alkylthio, provided that at least one of $R^2$ and $R^3$ is $C_{1-4}$ alkoxy, and $R^5$ is $C_{1-4}$ alkyl, and especially ethyl; and salts thereof.

Such compounds have a chiral centre at the 2-position of the pyrrolidine ring and can thus exist in isomeric form and racemic mixtures. As mentioned above the compounds are usually prepared as racemic mixtures which can be separated into the individual enantiomers, or, alternatively the enantiomers can be prepared by utilising optically active amines in the preparation of the compounds. The preferred enantiomer is the laevorotatory (—) form.

The invention also includes a process for producing a compound according to formula (I) above, which comprises reacting a compound of the formula

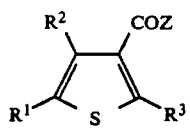

in which $R^1$, $R^2$ and $R^3$ have the values assigned them above, and Z is halo, —OH or —OR where R is a leaving group such as $C_{1-4}$ alkyl, with an amine of the formula $$XNH_2 \qquad\qquad (III)$$

in which X has the above-assigned values.

The reaction is preferably carried out at a temperature of from 0° C. to 200° C., more preferably from 0° C. to 100° C., in an inert organic solvent such as, for example a haloalkane, e.g. dichloromethane. When Z is —OH a coupling agent is preferably employed such as a coupling agent commonly used in peptide synthesis, for example carbonyldiimidazole. When Z is OR, it is often desirable to carry out the reaction at a higher temperature, for example from 100° C. to 200° C. The preferred reactions are those in which the reactant is one of formula (II) in which Z is halo or —OH.

Compounds of formula (II) are either readily available or can be prepared from known compounds by conventional synthesis. For example, base catalysed cyclisation of the appropriate thiodiacetate followed by aromatisation and alkylation or alkenylation gives compounds of formula (I) in which $R^2$ is $C_{1-4}$ alkoxy or $C_{2-4}$ alkenyloxy. Lithiation and carboxylation of the appropriate thiophene in which $R^3$ is $C_{1-4}$ alkoxy or $C_{2-4}$ alkenyloxy provides other compounds of formula (II). Methods of synthesis of such compounds are disclosed in "Thiophene and its Derivatives" Part 3 edited by Gronowitz, S., Wiley (New York) 1986 and the references therein.

The amine reactants of formula (III) are well known or are made by methods known in the art. For example, such cycloamine compounds are disclosed in J. Chem. Soc. (1957) 3165, South African Patent No. 69 00983, French Patent No. 2 534 255, and in Chemical Abstracts 66 2432 g (1967), and the 2-amino-8-aza nortropane starting reactants are disclosed in French Patent No. 2 499 570.

As will be appreciated it is possible to prepare some of the compounds of formula (I) by more than one route. When one or more of $R^1$, $R^2$ and $R^3$ is —CHO, —$CH_2OH$, —COOH, —$COC_{1-3}$ alkyl, —$CH(OH)C_{1-3}$ alkyl, $C_{1-4}$ alkylsulphinyl, $C_{1-4}$ alkylsulphonyl or optionally substituted phenylsulphinyl or phenylsulphonyl, the compound of formula (I) can be prepared by condensation of the intermediate of formula (II) in which $R^1$, $R^2$ and $R^3$ has the above-mentioned values (—COOH being suitably protected by an ester group), or alternatively, the condensation reaction can be carried out on the appropriate intermediate in which $R^1$, $R_2$ and $R^3$ is $C_{1-4}$ alkyl, $C_{1-4}$ alkylthio or optionally substituted phenylthio, and the product of condensation submitted to oxidation employing, for example, a $Ce^{IV}$ oxidising agent such as cerium ammonium nitrate or cerium sulphate to oxidise a methyl group to —CHO and —COOH or a higher alkyl group to —$COC_{1-3}$ alkyl. $C_{1-4}$ Alkylthio and phenylthio groups can be converted to the sulphinyl and sulphonyl derivatives with oxidising agents such as for example meta-chloroperbenzoic acid. Compounds in which $R^1$, $R^2$ or $R^3$ are —$CH_2OH$ or —$CH(OH)C_{1-3}$ alkyl can be prepared by reducing the corresponding aldehyde and ketone derivaties, respectively, employing for example sodium borohydride or lithium aluminium hydride. Compounds in which there is a —$CH_2OC_{1-4}$ alkyl group can be readily derived from the hydroxymethyl compound by alkylation with, for example, alkyl iodide and base or trialkyloxonium tetrafluoroborate.

As mentioned above, the compounds of the invention in free base and pharmaceutically acceptable salt and ester forms have useful central nervous system activity. They are also of low toxicity. Their activity has been demonstrated by testing in animal models using well-established procedures. More specifically, the compounds have been shown to block apomorphine induced climbing in mice according to the method of Costall, Naylor and Nohria (European J. Pharmacol. 50, 39; 1978), and/or to block a conditioned avoidance response in rats according to the method of Jacobsen and Sonne (Acta Pharmacol. et Toxacol. 11, 35, 1955), at doses below 50 mg/kg when administered intraperitoneally.

These tests show that the compounds of the invention block post-synaptic dopamine receptors and are accordingly indicated for the treatment of emesis, depression, anxiety and psychotic conditions such as schizophrenia and acute mania.

The compounds are effective over a wide dosage range, the actual dose administered being dependent on such factors as the particular compound being used, the condition being treated and the type and size of mammal being treated. However, the dosage required will normally fall within the range of 0.05 to 10 mg/kg per day, for example in the treatment of adult humans dosages of from 0.2 to 5 mg/kg may be used.

The compounds and pharmaceutially-acceptable salts and esters of the invention will normally be administered orally or by injection and, for this purpose, the compounds, salts and esters will usually be utilised in the form of a pharmaceutical composition. Such compositions are prepared in a manner well known in the pharmaceutical art and normally comprise at least one active compound or pharmaceutically-acceptable salt or ester of the invention associated with a pharmaceutically-acceptable diluent or carrier therefor. Such compositions form part of the present invention. In making such compositions, the active ingredient will usually be mixed with a carrier or diluent. Additionally or alternatively it may be enclosed within a carrier which may be in the form of a capsule, sachet, paper or other container. When the carrier serves as a diluent, it may be a solid, semi-solid or liquid material which acts as a vehicle, excipient or medium for the active ingredient. Some examples of suitable carriers are lactose, dextrose, sucrose, sorbitol, mannitol, stargesh, gum acacia, calcium phospate, alginates, tragacanth, gelatin, syrup, methyl cellulose, methyl and propylhydroxybenzoate, talc, magnesium stearate or mineral oil. The compositions of the invention may, as is well-known in the art, be formulated so as to provide quick, sustained or delayed release of the active ingredient after administration to the patient.

Depending on the route of administration, the foregoing compositions may be formulated as tablets, capsules or suspensions for oral use or injectable solutions for parenteral use. Preferably the compositions are formulated in a dosage unit form, each dosage containing from 1 to 200 mg more usually 5 to 100 mg, of the active ingredient.

The invention is illustrated by the following Examples.

EXAMPLE 1

(a) 5-Chloro-4-methoxy-3-thiophenecarboxylic acid

To 4-methoxythiophene-3-carboxylic acid (3.16 g) in chloroform (10 ml) was added freshly distilled sulphuryl chloride (1.8 ml). After the exothermic reaction had subsided the product was extracted into 2N NaOH and washed with chloroform. The aqueous solution was acidified with 2N HCl and extracted into dichloromethane, washed with water, dried over magnesium sulphate and the solvent evaporated. The product was crystallised from dichloromethane/n-hexane.

(b) 5-Chloro-N-(2-diethylaminoethyl)-4-methoxythiophene-3-carboxamide

To carbonyl di-imidazole (800 mg) in tetrahydrofuran (25 ml) under a nitrogen atmosphere was added 5-chloro-4-methoxythiophene-3-carboxylic acid (960 mg). After stirring at ambient for 1 hour freshly redistilled N,N-diethylethylene diamine (0.75 ml) was added and the mixture stirred for 20 hours. The mixture was partitioned between 5M HCl and ethyl acetate. The acid solution was basified with 2N NaOH and extracted into dichloromethane, washed with water, dried over magnesium sulphate and the solvent evaporated to leave an oil. The base was converted to the fumarate salt crystallising from ethyl acetate.

Similarly prepared was: N-(2-diethylaminoethyl)-4-methoxythiophene-3-carboxamide.

EXAMPLE 2

(a) Methyl 4-methoxy-3-thiophenecarboxylate

The method of Press et al. (J. Org. Chem. (1979) 44 3292) was used, suitably modified as follows.

Methyl 4-hydroxy-2,5-dihydrothiophene-3-carboxylate (J. Am. Chem. Soc. (1946) 68 2232; Monatsh. Chem 1973) 104 1520) (32 g) was heated under reflux for 20 hours in isopropenyl acetate (75 ml) with p-toluene sulphonic acid (200 mg). The excess solvent was evaporated to leave a residue which was dissolved in dichloromethane (75 ml) and cooled to $-25°$ C. Sulphuryl chloride (16 ml) was added over 20 minutes and the mixture stirred at $-25°$ C. for 1.5 hours and then at $20°$ C. for 20 hours. The solvent was evaporated to leave a solid (40.4 g) which was refluxed in methanol (600 ml) with concentrated sulphuric acid (4 ml) for 48 hours. The solution was evaporated to a low bulk and partitioned between water and ethyl acetate. The organic phase was dried with magnesium sulphate, the solvent evaporated, and the product distilled b 0.04 mm $130°$ C.

(b) 4-Methoxy-3-thiophenecarboxylic acid

The above compound was prepared from methyl 4-methoxy-3-thiophenecarboxylate by the method of Press, Hofmann and Safu J. Org. Chem. (1979) 44 3292.

(c) N-[(1-Ethyl-2-pyrrolidino)methyl]-4-methoxythiophene-3-carboxamide

4-Methoxy-3-thiophenecarboxylic acid (800 mg) and carbonyl di-imidazole (800 mg) were stirred under a nitrogen atmosphere in tetrahydrofuran (50 ml) for 1.5 hours. 2-Amino-methyl-1-ethylpyrrolidine (640 mg) was added and the solution stirred for 20 hours and then partitioned between 2N HCl and dichloromethane. The acid solution was basified with 2N NaOH and extracted into dichloromethane, washed with water, dried with MgSO$_4$ and the solvent evaporated to leave the crude product as an oil, which was converted to the fumarate salt crystallising from ethyl acetate, m.p. 126°.

5-Chloro-N-[(1-ethyl-2-pyrrolidino)methyl]-4-methoxythiophene-3-carboxamide was similarly prepared m.p. 136° (ethyl acetate).

EXAMPLE 3

(a) Methyl 3-(2-carbomethoxyethyl)thiopropionate

To a solution of methyl mercapto propionate (66 g) in 51 ml of anhydrous methanol cooled at 0° C. was added 120 ml of a 25% solution of sodium methoxide in methanol. To this solution was added dropwise a solution of ethyl 2-bromopropionate (100 g) in 100 ml of anhydrous methanol.

The reaction mixture was stirred at room temperature for 20 hours and the solvent removed. The oily residue was dissolved in 300 ml of ether and washed with sodium bicarbonate (10% solution). The organic layer was dried over MgSO$_4$, filtered and the solvent removed, leaving a crude product which was used in the next step without further purification (see Swiss Patent No. 858012).

(b) Methyl 4-keto-5-methyl-2,3,4,5-tetrahydrothiophene-5-carboxylate

To a solution of α-methyl 3-(2-carbomethoxyethyl)-thiopropionate (112 g) in 86 ml of anhydrous benzene, was added dropwise a suspension of sodium methoxide (28.6 g) in 186 ml of anhydrous benzene.

The reaction mixture was stirred at room temperature over night, diluted with 300 ml of water and the solution extracted twice with ether (200 ml) and benzene (200 ml).

The aqueous layer was acidified with 6N HCl to pH1 and extracted with methylene chloride (300 ml×3). The organic layer was washed with brine, dried (Na$_2$SO$_4$) and the solvent removed. The oily residue was used in the next stage without further purification.

(c) Methyl 4-acetoxy-2,5-dihydro-5-methyl-3-thiophenecarboxylate

Methyl 4-keto-5-methyl-2,3,4,5-tetrahydrothiophene-3-carboxylate (90.83 g) and p-toluenesulphonic acid (1 g) were refluxed for 6 hours in isopropenyl acetate (214 ml) and then stood at room temperature for 22 hours.

Excess solvent was removed and the crude product used in the next step.

(d) Methyl 4-acetoxy-5-methyl-3-thiophenecarboxylate

To methyl 4-acetoxy-2,5-dihydro-5-methyl-3-thiophene-carboxylate (68.3 g) in anhydrous methylene chloride (143 ml) was added sulphuryl chloride (30.4 ml) dropwise over 30 minutes. The black solution was stirred at room temperature over night.

Excess reagent and solvent were removed and the residue was used without purification in the next step.

(e) Methyl 4-hydroxy-5-methyl-3-thiophenecarboxylate

To methyl 4-acetoxy-5-methyl-3-thiophenecarboxylate (214 g) in methanol (250 ml) was added p-toluenesulphonic acid (2 g), and the solution stirred at room temperature for three days.

Excess solvent were removed and the oily residue was dissolved in methylene chloride (250 ml), washed with sodium bicarbonate, dried (Na$_2$SO$_4$), filtered, and the solvent removed.

The residue was distilled, and the fraction boiling at 80° C./3 mm collected.

(f) Methyl 4-methoxy-5-methyl-3-thiophenecarboxylate

Methyl 4-hydroxy-5-methyl-3-thiophenecarboxylate (34 g), potassium carbonate (37 g) and dimethyl sulphate (33.67 g) were stirred in anhydrous acetone (200 ml) at room temperature for 20 days. The reaction mixture was filtered and the solvent removed.

The residue dissolved in methylene chloride (150 ml) was washed with distilled water (100 ml), dried (Na$_2$SO$_4$), filtered, and the solvent removed.

The oily residue was distilled and the fraction boiling at 74° C./2 mm collected.

(g) 4-Methoxy-5-methyl-3-thiophenecarboxylic acid

Methyl-4-methoxy-5-methyl-3-thiophenecarboxylate (10.4 g) dissolved in a solution of sodium hydroxide (6.7 g) in water (168 ml) was refluxed for 3 hours.

The clear solution was cooled to 0° C. and acidified to pH 5.5 with acetic acid and extracted with methylene chloride (3×50 ml).

The organic layer was washed with water (50 ml) dried (Na$_2$SO$_4$), filtered and the solvent removed. The residue was recrystallised from methylene chloride/ligroine, m.p. 123° C.

(h) (±)N-{(1-Ethyl-2-pyrrolidinyl)methyl}-4-methoxy-5-methylthiophene-3-carboxamide, fumarate To a solution of 4-methoxy-5-methyl-3-thiophenecarboxylic acid (2.06 g) in dry dichloromethane (80 ml) under nitrogen was added 1,1'carbonyldiimidazole (1.9 g). After stirring for 3 hours at room temperature, (±) 2-aminomethyl-1-ethylpyrrolidine (1.9 g) was added and the solution stirred at room temperature for 22 hours. The reaction mixture was extracted with 3N HCl (3×40 ml), the acid layer cooled and made alkaline by the addition of 5N NaOH and extracted with methylene chloride (3×30 mol). After drying (sodium sulphate) and evaporation of the solvent, the residual oil was dissolved in hot ethyl acetate (20 ml), and fumaric acid (1.39 g) was added. The fumarate salt was crystallised from the cooled solution and filtered, m.p. 137° C.

EXAMPLE 4

(a) Diethyl 3-hydroxy-5-methylthiothiophene-2,4-dicarboxylate

A mixture of diethylmalonate (4 g) and carbon disulphide (1.9 g) was added to a solution of potassium tert-.butoxide (5.6 g) in benzene (80 ml), keeping the temperature at 0° C. The mixture was stirred for two hours, ethyl chloroacetate (3 g) was added at 0° C. and after stirring for 1 hour, methyl iodide (3.55 g) was added.

This solution was stirred at room temperature for two hours, and then poured into water. The organic layer was separated and, after evaporation of solvent, ethanol (30 ml) and sodium ethoxide (0.0189 mol) was added. After stirring for two hours at room temperature, the solution was acidified with 10% hydrochloric acid, the precipitate filtered and recrystallised from ethanol, m.p. 109°–110° C.

(b) Diethyl 3-methoxy-5-methyl-thiophene-2,4-dicarboxylate

Dimethyl sulphate (0.38 g) was added to a stirred mixture of the hydroxythiophene (0.8 g) and potassium carbonate (0.42 g) in 2-butanone. The mixture was heated under reflux for 6 hours. The solvent was removed and the residue partitioned between water and ethyl acetate. The organic layer was dried over sodium sulphate and the solvent evaporated. The residue was recrystallised from ethanol, m.p. 109°–111° C.

(c) 3-Methoxy-5-methylthiothiophene-2,4-dicarboxylic acid

The diethyl ester of (b) above (0.4 g) was suspended in 5.3 ml of 1N sodium hydroxide solution and heated under reflux for 90 minutes. The mixture was cooled and acidified with dilute hydrochloric acid, and extracted with ethyl acetate. The organic extract was dried over sodium sulphate and the solvent evaporated.

The dicarboxylic acid thus formed was used in the next step without further purification.

(d) 4-Methoxy-2-methylthiothiophene-3-carboxylic acid

The dicarboxylic acid of (c) above (0.3 g) was sublimed at 200° C., 0.5 mm Hg and the product thus obtained recrystallised from benzene, m.p. 130°–131° C.

(e) 5-Chloro-4-methoxy-2-methylthiothiophene-3-carboxylic acid

Equimolecular amounts of the thiophene (d) above and N-chlorosuccinimide were dissolved in 1/1 chloroform/acetic acid mixture. The mixture was stirred for two hours and then poured into water. The organic layer was washed with 10% aqueous sodium hydroxide, dried over sodium sulphate and the solvent evaporated. The carboxylic acid was purified by recrystallisation from ethanol, m.p. 193°–194° C.

(f) (±) 5-Chloro-N-{(1-ethyl-2-pyrrolidinyl)methyl}-4-methoxy-2-methylthio-3-carboxamide, fumarate To a solution of the thiophene-3-carboxylic acid of (d) above (0.012 mol) in dry dichloromethane (80 ml) under nitrogen was added carbonyldiimidazole (1.9 g). After stirring for 1 hour at room temperature, (±)-2-aminomethyl-1-ethylpyrrolidine (0.012 mol) was added and the solution stirred at room temperature over night.

The reaction mixture was extracted with 3N hydrochloric acid, and the organic layer washed with aqueous sodium hydroxide solution and water. After drying over sodium sulphate, the solvent was evaporated under reduced pressure. The oil thus obtained was dissolved in hot ethyl acetate and fumaric acid (equimolecular amount) was added.

The fumarate salt crystallised from the cooled solution and was removed by filtration, m.p. 125°–128° C.

Similarly prepared was (±) N-{(1-ethyl-2-pyrrolidinyl)methyl}-4-methoxy-2-methylthio-3-carboxamide, fumarate, m.p. 137°–141° C.

The following Examples illustrate the preparation of typical formulations containing an active ingredient according to the invention.

EXAMPLE 5

Hard Gelatin Capsule

Each capsule contains

| Active ingredient | 10 mg |
|---|---|
| PEG 4000 | 250 mg |

The PEG 4000 is melted and mixed with the active ingredient. Whilst still molten the mixture is filled into capsule shells and allowed to cool.

EXAMPLE 6

Tablet

Each tablet contains

| Active ingredient | 10 mg |
|---|---|
| Calcium carbonate | 300 mg |
| Magnesium stearate | 10 mg |
| Starch | 30 mg |
| Hydroxypropylmethylcellulose | 10 mg |
| Iron Oxide | 4 mg |

The active ingredient is granulated with calcium carbonate and starch. The dried granulate is blended with lubricant and disintegrant and compressed into tablets of the required dosage strength. The tablet may then be coated.

EXAMPLE 7

Injection

| Active ingredient | 10 mg |
|---|---|
| Water | 1 mg |

The active ingredient is dissolved in water and distributed into vials, ampoules or pre-pack syringes using appropriate equipment. The product is sterilised.

We claim:
1. A compound of the formula

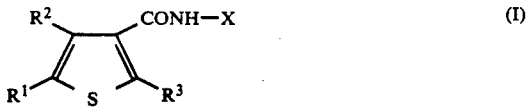

in which $R^1$, $R^2$ and $R^3$ independently are hydrogen, hydroxy, halo, nitro, amino, $C_{2-5}$ acylamino, $C_{1-4}$ alkyl, —CHO, —CH$_2$OH, —CH$_2$OC$_{1-4}$ alkyl, —COOH, —COC$_{1-3}$ alkyl, —CH(OH)C$_{1-3}$ alkyl, $C_{1-4}$ alkoxy, $C_{2-4}$ alkenyloxy, $C_{1-4}$ alkylthio, $C_{1-4}$ alkylsulphinyl, $C_{1-4}$ alkylsulphonyl, N-substituted heterocyclyl, optionally substituted phenyl, optionally substituted phenylthio, optionally substituted phenylsulphinyl, optionally substituted phenylsulphonyl or optionally substituted phenylsulphonamido, or $R^1$ and $R^2$ together form a $C_{3-5}$ alkylene bridge; provided that at least one of $R^2$ and $R^3$ is $C_{1-4}$ alkoxy or $C_{2-4}$ alkenyloxy; and X is (i) —(CH$_2$)$_n$N(R$^4$)$_2$ where each 'R$^4$ independently is $C_{1-4}$ alkyl, $C_{2-4}$ alkenyl or optionally substituted C$_6$H$_5$CH$_2$—, and n is 1, 2 or 3, or (ii) a 5- to 8-membered alicyclic group containing one or two nitrogen atoms and directly attached to the amido nitrogen or attached by a $C_{1-3}$ alkylene chain; and salts and esters thereof.

2. A compound according to claim 1 in which X is a group of the formula

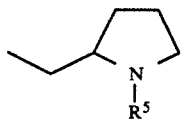

in which $R^5$ is $C_{1-4}$ alkyl.

3. A compound according to claim 2 in which $R^1$, $R^2$ and $R^3$ independently are hydrogen, halo, —CHO, $CH_2OH$, $C_{1-4}$ alkyl, $C_{1-4}$ alkoxy or $C_{1-4}$ alkylthio, provided that at least one of $R^2$ and $R^3$ is $C_{1-4}$ alkoxy.

4. A pharmaceutical formulation comprising a compound according to claim 1 or a pharmaceutically-acceptable salt or ester thereof and a pharmaceutically-acceptable diluent or carrier therefor.

5. A method of treating an animal, including a human, suffering from or susceptible to a disorder of the central nervous system, which comprises administering an effective amount of a compound according to claim 1, or a pharmaceutically-acceptable salt or ester thereof.

* * * * *